(12) United States Patent
Auxier et al.

(10) Patent No.: US 10,041,890 B2
(45) Date of Patent: Aug. 7, 2018

(54) RADIOPAQUE PROTECTIVE FILL FOR MANUFACTURE, REPAIR, OR REMANUFACTURE OF COOLED COMPONENTS

(71) Applicant: UNITED TECHNOLOGIES CORPORATION, Hartford, CT (US)

(72) Inventors: James Tilsley Auxier, Bloomfield, CT (US); Lea Kennard Castle, Vernon, CT (US)

(73) Assignee: United Technologies Corporation, Farmington, CT (US)

( * ) Notice: Subject to any disclaimer, the term of this patent is extended or adjusted under 35 U.S.C. 154(b) by 345 days.

(21) Appl. No.: 14/817,422

(22) Filed: Aug. 4, 2015

(65) Prior Publication Data

US 2017/0038312 A1    Feb. 9, 2017

(51) Int. Cl.
*G01J 1/42* (2006.01)
*G01N 23/00* (2006.01)
*B22C 1/02* (2006.01)
*B22C 9/10* (2006.01)
*B22D 29/00* (2006.01)
*B22D 46/00* (2006.01)
(Continued)

(52) U.S. Cl.
CPC .............. *G01N 23/00* (2013.01); *B22C 1/02* (2013.01); *B22C 9/10* (2013.01); *B22C 9/103* (2013.01); *B22C 9/105* (2013.01); *B22C 9/24* (2013.01); *B22D 29/001* (2013.01); *B22D 29/005* (2013.01); *B22D 46/00* (2013.01); *B23K 26/18* (2013.01); *B23K 26/389* (2015.10); *F01D 5/005* (2013.01); *G01M 15/14* (2013.01); *B23K 2201/001* (2013.01)

(58) Field of Classification Search
CPC ........................................................ G01N 23/00
USPC ............................................................ 250/395
See application file for complete search history.

(56) References Cited

U.S. PATENT DOCUMENTS 4,093,017 A    6/1978 Miller et al.
4,799,530 A *  1/1989 Sturgis ..................... B22C 1/00
                                                    164/5
(Continued)

FOREIGN PATENT DOCUMENTS

EP    0914884 A1    5/1999
EP    2078578 A1    7/2009
(Continued)

OTHER PUBLICATIONS

European Extended Search Report dated Nov. 29, 2016, issued in the corresponding European Patent Application No. 16182883.5.

*Primary Examiner* — David Porta
*Assistant Examiner* — Meenakshi Sahu
(74) *Attorney, Agent, or Firm* — Bachman & LaPointe, P.C.

(57) ABSTRACT

A method of manufacturing a core for casting a component can include manufacturing a core for at least partially forming an internal passage architecture of a component with a material including radiopaque particles. A method can include removing a material including radio opaque particles from an internal passage architecture of a component; and inspecting the component via radiographic imaging at gamma/X-ray wavelengths to detect residual material. A core for use in casting an internal passage architecture of a component can include a material with radiopaque particles dispersed therein.

27 Claims, 5 Drawing Sheets

(51) Int. Cl.
*F01D 5/00* (2006.01)
*G01M 15/14* (2006.01)
*B22C 9/24* (2006.01)
*B23K 26/18* (2006.01)
*B23K 26/382* (2014.01)
*B23K 101/00* (2006.01)

(56) References Cited

U.S. PATENT DOCUMENTS

| | | |
|---|---|---|
| 5,626,988 A | 5/1997 | Daniel-Ivad et al. |
| 5,952,042 A | 9/1999 | Rafferty et al. |
| 6,394,750 B1 | 5/2002 | Hiskes |
| 6,402,866 B1 | 6/2002 | Casey et al. |
| 6,503,349 B2 | 1/2003 | Pietruska et al. |
| 6,589,600 B1 | 7/2003 | Hasz et al. |
| 6,612,480 B1 | 9/2003 | Rafferty |
| 6,797,759 B1 | 9/2004 | Ellison et al. |
| 6,909,800 B2 | 6/2005 | Vaidyanathan |
| 7,207,374 B2 | 4/2007 | Persky et al. |
| 7,259,350 B2 | 8/2007 | Minor et al. |
| 7,388,980 B2 | 6/2008 | Vaidyanathan |
| 7,966,707 B2 | 6/2011 | Szela et al. |
| 8,394,215 B2 | 3/2013 | Abriles et al. |
| 2003/0106215 A1* | 6/2003 | Heyward ............ B23P 6/002 29/889.1 |
| 2004/0238596 A1 | 12/2004 | Ellison et al. |
| 2005/0098296 A1* | 5/2005 | Beals ................ B22C 9/10 164/369 |
| 2011/0189440 A1* | 8/2011 | Appleby ............ B22C 9/04 428/156 |
| 2014/0166255 A1 | 6/2014 | Bogue et al. |
| 2015/0078958 A1 | 3/2015 | Bewlay et al. |

FOREIGN PATENT DOCUMENTS

| | | |
|---|---|---|
| GB | 2053244 A | 2/1981 |
| WO | 2015009448 A1 | 1/2015 |

* cited by examiner

RADIOPAQUE PROTECTIVE FILL FOR MANUFACTURE, REPAIR, OR REMANUFACTURE OF COOLED COMPONENTS

BACKGROUND

The present disclosure relates generally to a radiopaque material and, more particularly, to processes for inspecting components.

Gas turbine engines, such as those that power modern commercial and military aircraft, generally include a compressor section to pressurize an airflow, a combustor section to burn a hydrocarbon fuel in the presence of the pressurized air, and a turbine section to extract energy from the resultant combustion gases.

Gas turbine engine hot section components such as blades and vanes are subject to high thermal loads for prolonged time periods. Other components also experience high thermal loads such as combustor, exhaust liner, blade outer air seal, and nozzle components. Historically, such components have implemented various air-cooling arrangements that permit the passage of air to facilitate cooling. In addition, the components are typically provided with various coatings such as thermal barrier coatings to further resist the thermal loads.

The internal passage architecture may be produced through various processes such as investment cast, die cast, drill, Electron Discharge Machining ("EDM"), milling, welding, additive manufacturing, etc. Investment casting is a commonly used technique for forming metallic components having complex geometries, especially hollow components, and is used in the fabrication of superalloy gas turbine engine components.

A ceramic core is typically used in the manufacturing process to form the hollow internal cavities therein. Oftentimes, manufacture, repair, and/or remanufacture, requires formation of an internal cavity and/or protection thereof from harsh chemicals to prevent internal surfaces from being coated, and/or to facilitate non-destructive testing techniques. Various processes may require temperatures that may be near the alloy incipient melting point as well as utilize reactive chemicals which may limit the choice of fill materials.

The core may be leached out of the component by dissolution or other reactive erosion method subsequent to manufacture, repair, and/or remanufacture. Single-crystal superalloy casting is typically leached of an alumina or silica-base ceramic core by flushing with a caustic solution. This leaching process may not always be successful in the complete removal of the core, which may affect the function of the final component through distortion of the internal passage architecture. As such, the component is typically inspected via a neutron radiography ("N-ray"), where neutrons are utilized to substantially penetrate the metal casting but are more attenuated by tagging agents that bind to residual core material that remain within the internal passage architecture after the leaching process. This N-ray process, although effective, is relatively expensive and complex as a nuclear reactor or particle accelerator is required to produce a sufficient neutron source.

SUMMARY

A method of manufacturing a core for casting a component according to one disclosed non-limiting embodiment of the present disclosure can include manufacturing a core for at least partially forming an internal passage architecture of a component with a material including radiopaque particles.

A further embodiment of the present disclosure may include, wherein the radiopaque particles include refractory metal oxide particles.

A further embodiment of the present disclosure may include, wherein the radiopaque particles include at least one of Molybdenum Dioxide ($MoO_2$), Zirconium Dioxide ($ZrO_2$), tungsten trioxide, tantalum pentoxide, molybdenum silicide, tungsten silicide, elemental molybdenum, tantalum, chromium and tungsten.

A further embodiment of the present disclosure may include inspecting the component via radiographic imaging at gamma/X-ray wavelengths to detect residual material subsequent to manufacture of the component.

A further embodiment of the present disclosure may include, wherein manufacturing the core include attaching a Refractory Metal Core to the core.

A further embodiment of the present disclosure may include, wherein the core is produced by a molding process.

A further embodiment of the present disclosure may include, wherein the core is transfer molded.

A further embodiment of the present disclosure may include, wherein the core is injection molded.

A further embodiment of the present disclosure may include, wherein the core is additively manufactured.

A further embodiment of the present disclosure may include an outer shell mold that contains the core, wherein a cavity is formed by the outer shell mold and the core, the cavity defining the component.

A method according to another disclosed non-limiting embodiment of the present disclosure can include removing a material including radio opaque particles from an internal passage architecture of a component; and inspecting the component via radiographic imaging at gamma/X-ray wavelengths to detect residual material.

A further embodiment of the present disclosure may include, wherein the radiopaque particles include refractory metal oxide particles.

A further embodiment of the present disclosure may include, wherein the radiopaque particles include at least one of Molybdenum Dioxide ($MoO_2$), Zirconium Dioxide ($ZrO_2$), tungsten trioxide, tantalum pentoxide, molybdenum silicide, tungsten silicide, elemental molybdenum, tantalum, chromium and tungsten.

A further embodiment of the present disclosure may include filling at least one of a multiple of cooling holes formed by the internal passage architecture with the material.

A further embodiment of the present disclosure may include removing the material from the at least one of the multiple of cooling holes formed by the internal passage architecture with a manual operation.

A further embodiment of the present disclosure may include filling the at least one of the multiple of cooling holes formed by the internal passage architecture with an Oxidation Resistant Braze (ORB).

A further embodiment of the present disclosure may include forming a cooling hole through the Oxidation Resistant Braze (ORB) subsequent to the filling the at least one of the multiple of cooling holes formed by the internal passage architecture with an Oxidation Resistant Braze (ORB).

A core for use in casting an internal passage architecture of a component, according to another disclosed non-limiting embodiment of the present disclosure can include a material with radiopaque particles dispersed therein.

A further embodiment of the present disclosure may include, wherein the radiopaque particles include at least one of Molybdenum Dioxide (MoO2), Zirconium Dioxide (ZrO2), tungsten trioxide, tantalum pentoxide, molybdenum silicide, tungsten silicide, elemental molybdenum, tantalum, chromium and tungsten.

A further embodiment of the present disclosure may include, wherein the radiopaque particles includes refractory metal oxide particles.

The foregoing features and elements may be combined in various combinations without exclusivity, unless expressly indicated otherwise. These features and elements as well as the operation of the invention will become more apparent in light of the following description and the accompanying drawings. It should be understood, however, the following description and drawings are intended to be exemplary in nature and non-limiting.

BRIEF DESCRIPTION OF THE DRAWINGS

Various features will become apparent to those skilled in the art from the following detailed description of the disclosed non-limiting embodiment. The drawings that accompany the detailed description can be briefly described as follows.

DETAILED DESCRIPTION

Figure 1:
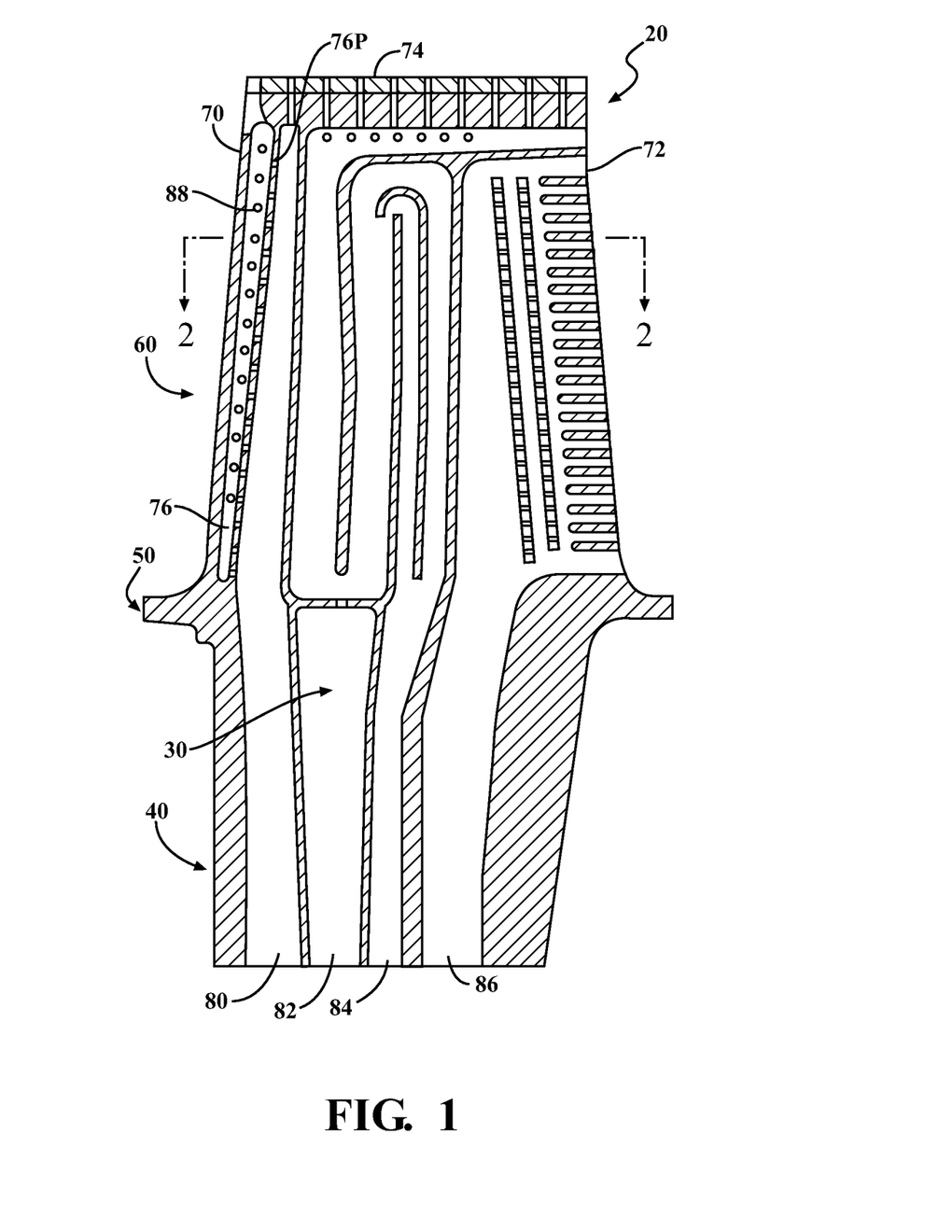
FIG. 1 is a general schematic view of an exemplary actively cooled component as a representative workpiece.
Figure 2:
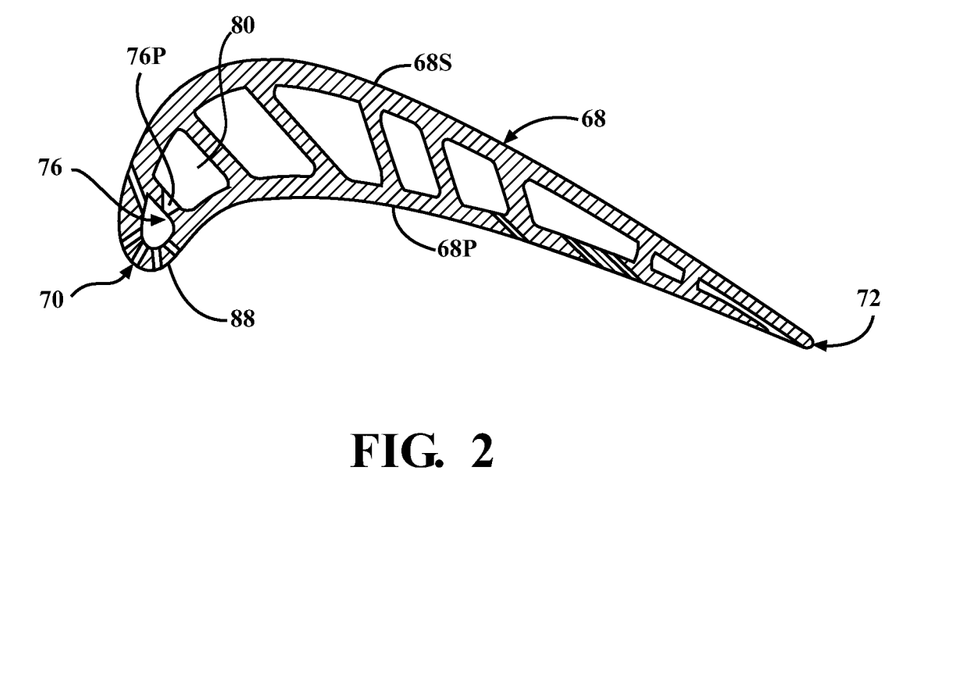
FIG. 2 is an expanded cross section of the actively cooled component along the line 2-2 of FIG. 1.

FIG. 1 schematically illustrates a general perspective view of an exemplary component 20, e.g., an actively cooled airfoil segment of a gas turbine engine. FIG. 2 is an expanded cross-sectional view of the component 20 along the line 2-2 of FIG. 1. It should be appreciated that although a particular component type is illustrated in the disclosed non-limiting embodiment, other components, such as blades, vanes, exhaust duct liners, nozzle flaps, and nozzle seals, as well as other actively cooled components will also benefit herefrom. These components, for example, operate in challenging high-temperature environments such as a hot section of a gas turbine engine and have aggressive requirements in terms of durability and temperature allowances.

The component 20 includes an internal passage architecture 30. The internal passage architecture 30 may include various passages, apertures and features. In this example, the component 20 may be a rotor blade that generally includes a root section 40, a platform section 50 and an airfoil section 60. The airfoil section 60 is defined by an outer airfoil wall surface 68 between a leading edge 70 and a trailing edge 72, as shown in FIG. 2. The outer airfoil wall surface 68 defines a generally concave shaped portion forming a pressure side 68P and a generally convex shaped portion forming a suction side 68S typically shaped for use in a respective stage of a high pressure turbine section.

The outer airfoil wall surface 68 extends spanwise from the platform section 50 to a tip 74 of the airfoil section 60. The trailing edge 72 is spaced chordwise from the leading edge 70. The airfoil has a multiple of cavities or passages for cooling air as represented by the leading edge passage 76 and supply passages 80, 82, 84, 86 which may extend through the root section 40. The passages extend into the interior of the airfoil section 60 and may extend in a serpentine or other non-linear fashion. It should be appreciated that the passage arrangement shown in FIGS. 1 and 2 is merely illustrative and that various passages may alternatively or additionally be provided.

A multiple of internal impingement holes, as represented by the hole 76P, fluidly connect the leading edge passage 76 in the leading edge region with the supply passage 80 to receive cooling air from the root section 40. It should be appreciated that the holes may be of various shapes. A multiple of film cooling holes adjacent the leading edge 70, as represented by the cooling holes 88, may extend from the leading edge passage 76 through the outer airfoil wall surface 68. The cooling holes 88, film or effusion, may be formed with, for example, lasers, Electron Discharge Machining ("EDM"), water jet, or other techniques. In a non-limiting example, the cooling holes 88 may be approximately 0.014-0.125 inches (0.35-3.2 mm) in diameter and may be drilled normal or angled to the outer airfoil wall surface 68.

Figure 3:
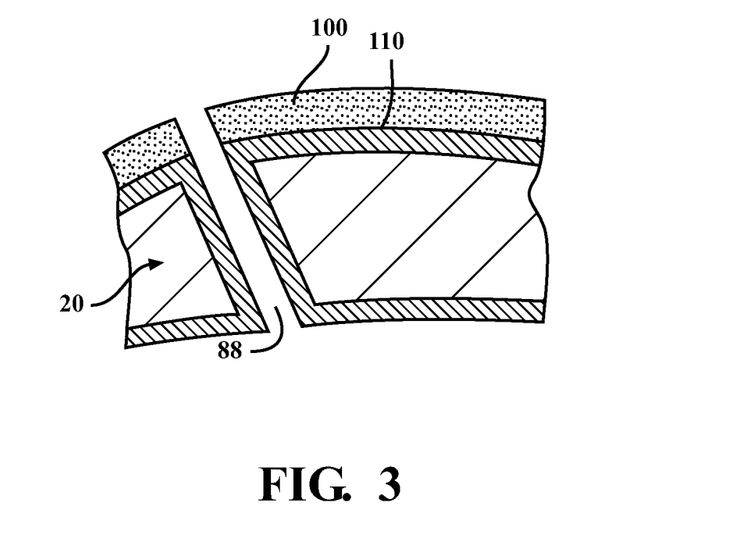
FIG. 3 is a sectional view of a coating on the component of FIG. 1.

With further reference to FIG. 3, the flow path surfaces of the component 20, such as the pressure side 68P and the suction side 68S (FIG. 2) of the airfoil section 60 and the associated surfaces of the platforms section 50 (FIG. 1), may be coated to provide thermal barrier, environmental barrier, and/or other capabilities required to survive in a high-temperature environment. The coating may be a thermal barrier coating that includes a bond coat 110 and a top coat 100. The bond coat 110, in one non-limiting example, may be a nickel-based alloy material which coats the pressure side 68P and the suction side 68S as well as the internal passage architecture 30 via immersion application, while the top coat 100 may be a ceramic material that is applied to the pressure side 68P and the suction side 68S via a plasma or other spray coating system. In some non-limiting embodiments, the top coat 100 may be thicker than the bond coat 110.

Figure 4:
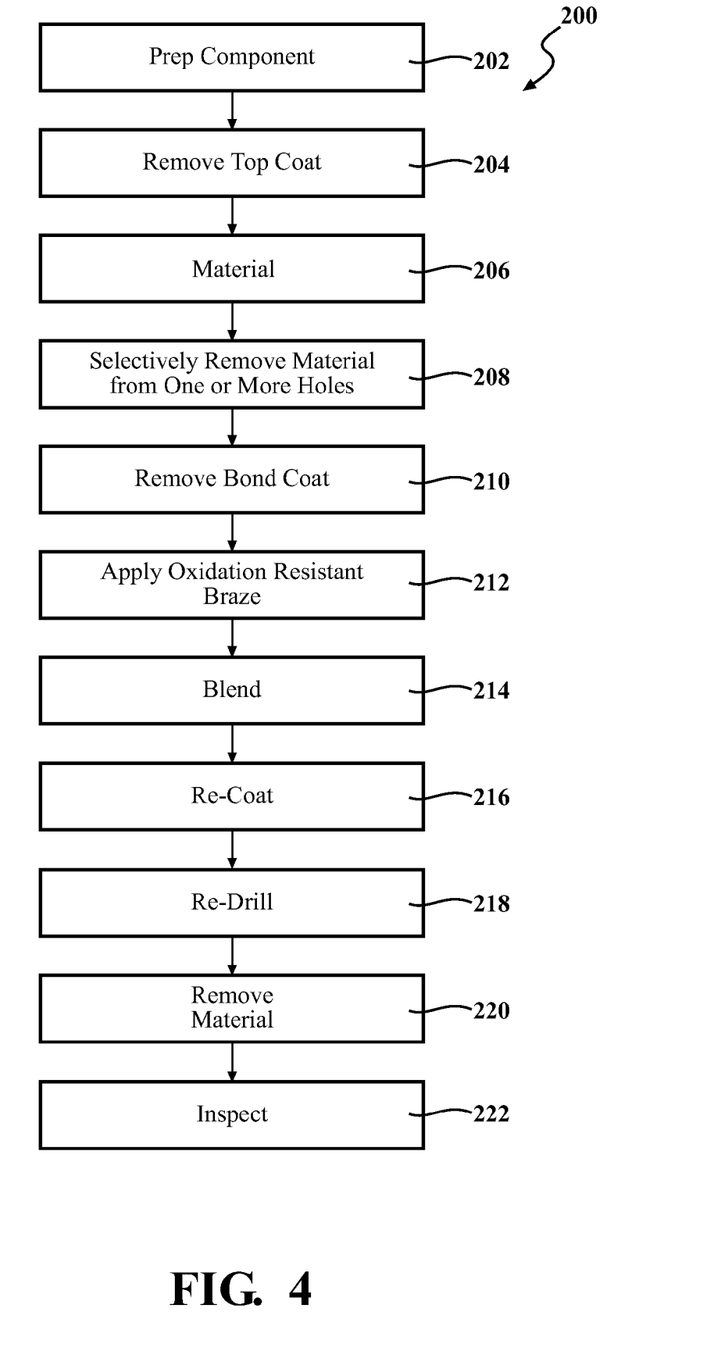
FIG. 4 is a flow diagram of a method of remanufacturing an actively cooled component utilizing a material that includes radiopaque particles according to a non-liming embodiment.

With reference to FIG. 4, a remanufacture method 200 in one disclosed non-limiting embodiment to restore the component 20 to near-original capability is shown. It should be appreciated that although a particular remanufacture method is depicted, other manufacture, repair, and/or remanufacture processes and methods will also benefit herefrom.

The method 200 initially includes preparation of the component 20 (step 202) such as by degreasing, fluoride-ion cleaning, grit blasting, hydrogen furnace cleaning, vacuum cleaning, and/or other processes. It should be appreciated that alternative or additional cleaning and preparation steps to facilitate the method may be performed.

Next, the top coat 100 may be removed (step 204). The removal or "strip" may be performed by a water jet, grit blast, potassium hydroxide, sodium hydroxide, or other process. The top coat 100 and a portion of the bond coat 110 may be removed. That is, the top coat 100 and the bond coat 110 are typically applied in sprayed layers such that all layers of the top coat 100 are removed and one or more of the layers of bond coat 110 may be removed in an area to be remanufactured. Alternatively, the entire top coat 100 is removed from the bond coat 110. Alternatively, still, the top coat 100 and the bond coat 110 may be completely removed.

Figure 5:
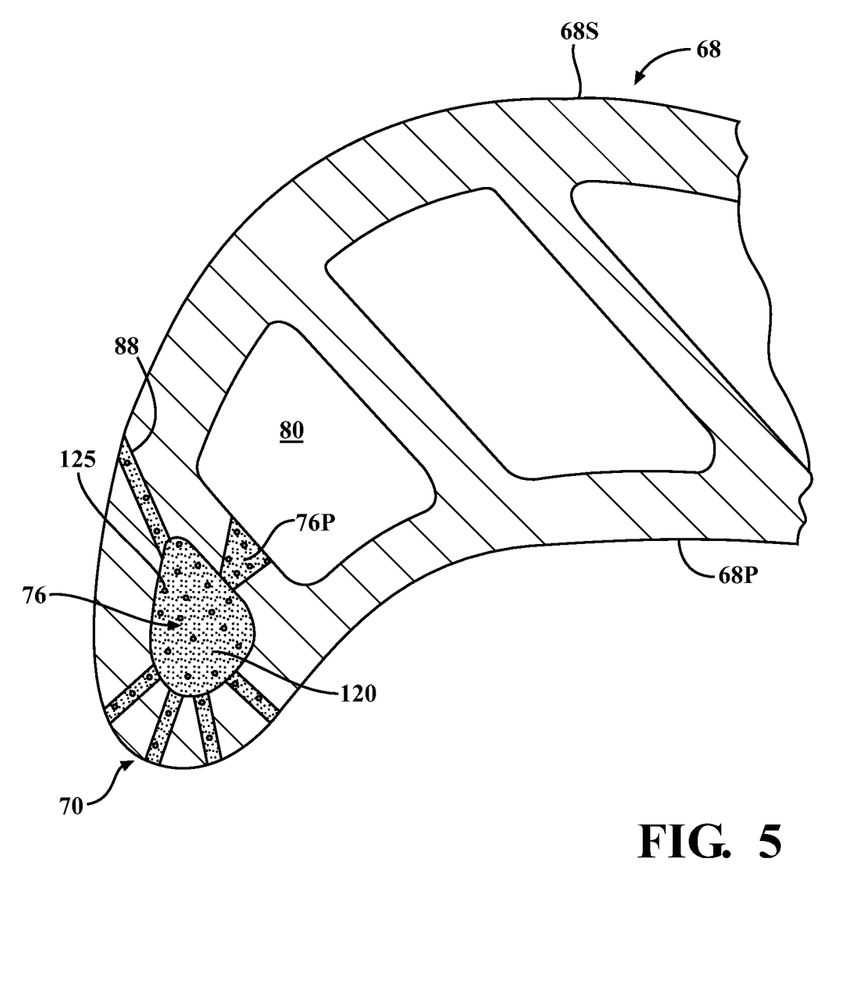
FIG. 5 is an expanded cross section of an actively cooled component representative of one step of the method of FIG. 4.

Next, a material 120 is disposed in the internal passage architecture 30 of the component (step 206; FIG. 5). The material 120 may be located in one or more passages such as the leading edge passage 76 or selectively disposed in only those passages that communicate with cooling holes 88 that extend through the outer airfoil wall surface 68. It should be appreciated that the material 120 may be utilized to form ceramic cores or other components that may be utilized to initially form the internal passage architecture 30 via, for example, a lost wax investment casting process as will be further described. In one embodiment, the material 120 may be an alumina or silica-base ceramic fill. In another embodiment, the material 120 may be a salt-based protective fill that is a water soluble material composed of a salt such as magnesium sulfate, tribasic potassium phosphate, or other such salt-based composition, that, in one specific example, may be a mixture of about 50 mol % of Na2CO3, about 20 mol % of NaCl, and about 30 mol % of KCl, which may be typical of a salt core casting material that is often utilized in an investment casting technique using water soluble cores composed of salts in place of the ceramic cores traditionally used in airfoil casting for generating internal cavities.

The salt-based protective fill may be injected into the internal passage architecture 30 as a slurry substance which hardens when cured. The upper temperature limit of the material 120 may be tuned by selection of the salt; for instance, magnesium sulfate will not melt until 2055° F. (1124° C.) and tribasic potassium phosphate will not melt until 2516° F. (1380° C.). While these melting temperatures are below ceramics, they offer a distinct advantage of being highly water-soluble: 255 g/L for magnesium sulfate and 900 g/L for tribasic potassium phosphate at 77° F. (25° C.) (as a reference, NaCl is water soluble at 350 g/L at 77° F. (25° C.)). The water-soluble, high-temperature-capable material 120 protects the internal passage architecture 30 during cooling hole repair, and facilitates a thermally and geometrically stable substrate for accurate braze repair of cooling holes 88.

Next, the cured material 120 may be selectively removed from within the holes 88 (step 208). The removal may be performed manually with a pick or other tool. That is, one or more holes 88 that are incorrectly positioned or otherwise to be filled may be cleaned of the material 120.

Next, the bond coat 110 is removed (step 210) via, for example, a hydrofluoric acid, or other process. The component 20 is typically dipped into the hydrofluoric acid. As the material 120 is disposed in the internal passage architecture 30, the material 120 operates to protect the internal passage architecture 30 from the hydrofluoric acid. That is, the material 120 operates to protect the bond coat 110 within the internal passage architecture 30.

Next, a nickel braze alloy composition such as an Oxidation Resistant Braze (ORB) composition is then applied to the component 20 over the holes 88 which are to be filled (step 212). An example of an Oxidation Resistant Braze ("ORB") composition is available under the trademark TURBOFIX. The nickel braze alloy composition is compatible with the nickel based superalloy that forms the component 20 as, in one example, the component 20 is formed of a nickel based superalloy known by the industry specification as a PWA 1455 base alloy.

The nickel braze alloy composition, in one disclosed non-limiting embodiment, includes a combination of: base powder alloy; alloy powder with a melting point depressant such as boron; and a braze binder such as an organic vehicle like cellulose. For example, the nickel braze alloy composition may include 50-80% base powder alloy and 10% braze binder with the remainder as an alloy powder with a melting point depressant. Various other combinations and ingredients may alternatively or additionally be utilized. The water-soluble, high-temperature-capable material 120 facilitates a thermally and geometrically stable substrate for accurate braze repair.

Next, the ORB may be blended into the substrate (Step 214).

Next, the component 20 may be recoated as required to repair the thermal barrier coating (step 216). That is, the bond coat 110 and the top coat 100 are reapplied as required. The removed layer(s) of bond coat 110 may be reapplied if necessary to bring the thickness of the bond coat 110 to specification. The bond coat 110 is relatively thin and reapplication thereof minimally effects, if at all, the cooling holes 88. The component 20 may then be cleaned and prepped if required to receive the top coat 100. The material 120, being high temperature resistant, facilitates the prevention of "coat down" in which prior coated holes 88 are undesirably reduced in diameter from their desired diameter in response to the recoating operation. That is, the material 120 may be maintained within the internal passage architecture 30 while the top coat 100 is applied.

Next, correctly positioned holes are drilled into the component 20 through the ORB (step 218). One process to form the holes is to laser drill each hole with a laser beam from the exterior of the outer airfoil wall surface 68. The material 120 operates to protect the internal passage architecture 30 to attenuate the intensity of the laser beam. The material 120 ensures that the laser beam does not inadvertently damage internal surfaces opposite the cooling air hole 88 after the laser beam breaks through the outer airfoil wall surface 68 during the laser drilling process.

The material 120 further facilitates the protection of features within the internal passage architecture 30 of a component 20 such as a turbine blade that is tuned, in this example, to maintain post-spall metal temperatures to be about 2000° F. (1093° C.). The post-spall metal temperatures difference for which the component 20 remains capable of resisting as compared to a remanufacture for which the features may be compromised are dependent upon the type of cavity and, for example, may be between about 20° F.-200° F. (−6° C.-93° C.) dependent upon the cavity configuration.

Finally, the material 120 is removed (step 220). The alumina or silica-base ceramic fill may be removed by flushing with a caustic solution. The salt-based protective fill does not require such relatively harsh solvents to remove, which may damage the underlying alloy and coating. In one example, an agitated water rinse is sufficient to remove the salt-based protective fill.

After the material 120 is removed (step 220), the component 20 may be inspected to ensure that the material 120 has been completed removed (step 222).

In one disclosed non-limiting embodiment, the material 120 includes radiopaque particles 125 (FIG. 5) that are sufficiently radiopaque to be used with more readily available gamma or X-ray techniques, as compared to N-ray techniques. The radiopaque particles 125 may include Molybdenum Dioxide (MoO2), Zirconium Dioxide (ZrO2), tungsten trioxide, tantalum pentoxide, molybdenum silicide, tungsten silicide, elemental molybdenum, tantalum, tungsten, and/or other refractory metal particles.

The main factors that contribute to a material's radiopacity are its density and atomic number. Refractory metals have one characteristic in common: an exceptionally high melting point. Although there are twelve refractory metals, only five are widely used: Tungsten, Molybdenum, Niobium, Tantalum and Rhenium. Refractory metal particles may be particularly beneficial as the radiopaque particles 125 as the refractory metal particles are readily capable of being milled down to desired particle sizes appropriate for typical ceramic injection molding. Refractory metal particles can also readily withstand the temperatures at which the filler material 120 are fired/sintered after injection to form the ceramic cores. In a non-limiting embodiment, the radiopaque particles 125 may be of particle sizes between about 0.0001 inches to 0.003 inches (0.0025 mm-0.076 mm) in diameter. It should be appreciated that radiopaque particles may be sized to be dispersed throughout the material 120 yet be visible in an X-ray or gamma ray image.

The radiopaque particles 125 may be dispersed within the material 120 when disposed in the internal passage architecture 30 (step 206; FIG. 4) to ensure detection during later inspecting via relatively available gamma or X-ray techniques. In one example, the radiopaque particles 125 may form between about 3-8% of the material 120. The quantity of radiopaque particles 125 may need only be limited to avoid defects in the material 120, e.g., that which cause defects to arise in the ceramic injection and firing process, such as, for example, cracking due to complications regarding sintering with other ceramic materials.

The refractory metal particles are highly radiopaque, exhibit virtually no chemical reactivity with agents used in the casting and manufacturing/repair processes, and can withstand temperatures far in excess of the range encountered in superalloy casting and manufacturing/repair processes before melting or decomposing. Being radiopaque, the refractory metal particles increase the bulk attenuation of the material 120 and thereby increase its ability to be detected via radiographic imaging at gamma/X-ray wavelengths during inspection to confirm the material 120 is completely removed without an increase in cost or lead time (step 222; FIG. 4).

The radiopaque particles 125 thus permit a film or digital X-ray, possibly a bench-top X-ray, to inspect components for residual material 120. With the X-ray and refractory metal doped core, any residual material after the removal process (step 220) would appear as a positive metal in the internal cavity. For example, the refractory metal may show up brighter (e.g., thicker material on wall of internal cavity) rather than darker (no material—empty internal cavity) on a gamma or X-ray image. This eliminates the heretofore need to use qualified nuclear reactors to inspect castings (e.g., N-ray inspection), which at times may be a single point of failure and industrial risk.

Figure 6:
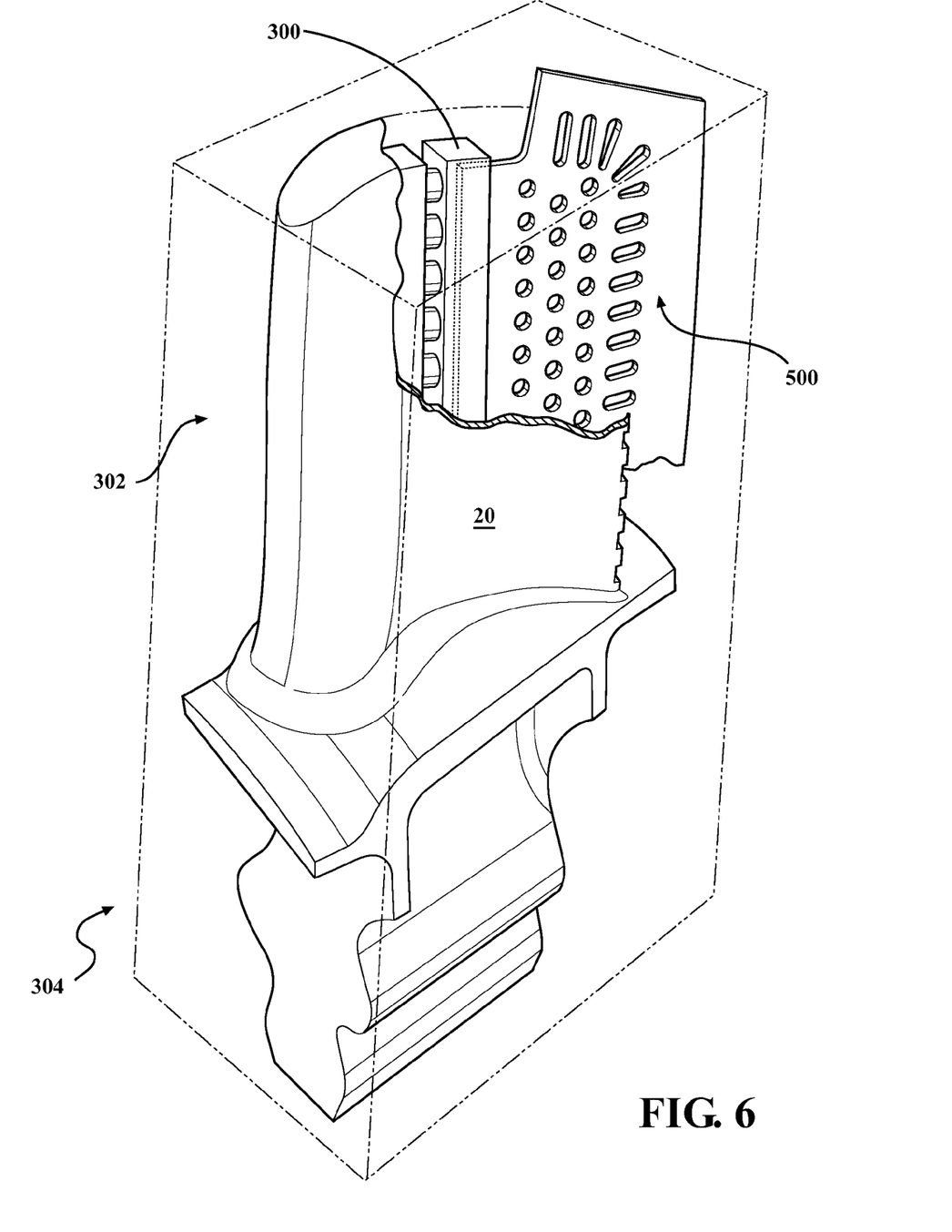
FIG. 6 is a schematic partial fragmentary view of a mold with a core formed of a material that includes radiopaque particles for casting of a component according to a non-liming embodiment.

With reference to FIG. 6, in another disclosed non-limiting embodiment, while not to be limited to any single method, a casting method may utilize a core 300 at least partially manufactured of the material 120 that includes radiopaque particles 125. The core 300 may be used in the manufacturing process of the component 20 to at least partially define the internal passage architecture 30 therein. That is, the core 300 is at least partially manufactured of the material 120 and may be utilized in an original manufacture type casting process.

The core 300 may be produced by a molding process using a ceramic slurry and a shaped die. It should be further appreciated that the material 120 including the radiopaque particles 125 may be injected, molded, transfer molded, additively manufactured, or otherwise manipulated to form the core 300. That is, irrespective of manufacture technique, the core 300 may be at least partially formed of the material 120 that includes the radiopaque particles 125. The radiopaque particles 125 may be dispersed within the material 120 upon manufacture of the core 300 to ensure detection during inspecting via relatively available gamma or X-ray techniques. As the radiopaque particles 125 can be dispersed within the material 120 when the core 300 is first formed, the core 300 is radiopaque from initial production, which enables inspection at any point in the process yet avoids harsh and toxic tagging chemicals as used in other processes.

The core 300 provides the geometry desired for the internal passage architecture 30 and is placed in a die whose walls surround, but are generally spaced away from, the core 300. The die is filled with a disposable pattern material such as wax, although plastics, low melting-point metals, and organic compounds such as urea, may be employed. The die is removed leaving the core 300 embedded in the disposable pattern material.

An outer shell mold 302 is then formed about the disposable pattern material by dipping the pattern in ceramic slurry and then applying larger, dry ceramic particles to the slurry. This process is termed stuccoing. The stuccoed wax pattern that contains the core 300 is then dried and the stuccoing process repeated to provide the desired wall thickness for the outer shell mold 302. At this point, the outer shell mold 302 is thoroughly dried and heated to an elevated temperature to remove the disposable pattern material, e.g., wax, and strengthen the ceramic material.

The result is a mold 304 formed by the outer shell mold 302 containing the core 300 therein and defining a mold cavity to cast the component 20. The exterior of the core 300 defines the internal passage architecture 30 to be formed in the cast component 20 and the interior of the outer shell mold 302 defines the external dimensions of the component 20. That is, the mold 304 operates as a melting unit and/or a die for a desired material that forms the component 20. The core 300 and outer shell mold 302 may also define casting portions such as gates and risers which are necessary for the casting process but are not a part of the finished cast component.

After the removal of the wax disposable pattern material and mold 304 is formed, a molten material is poured into the cavity and solidified. The desired material may include, but not be limited to, a superalloy or other material such as nickel based superalloy, cobalt based superalloy, iron based superalloy, and mixtures and/or alternatives thereof that is melted; a molten superalloy that is then solidified; or other material. Alternatively, or in addition, a single crystal starter seed or grain selector may be utilized to enable a single crystal to form when solidifying the component. During the casting process, the core 300 fills a selected volume within the outer shell mold 302 that, when removed from the finished casting, defines the internal passage architecture 30 utilized for cooling airflow within the component 20.

Alternatively, or in addition, the core 300 may optionally include a Refractory Metal Core (RMC) 500 mounted thereto to form a portion of the internal passage architecture 30. RMC 500, in some embodiments, can be a metal based sheet with a protective coating. The RMC 500, in one example, is a sheet with apertures that forms a thin portion of a trailing edge cavity with features formed by the apertures.

The refractory metal of RMC 500 provides more ductility than conventional ceramic core materials while the coating protects the base metal from alloying with the refractory metal in the investment casting process. The RMC 500 may be attached to the core 300 via an adhesive or other attachment mechanism to form a portion of the internal passage architecture 30 such as that which is contiguous to the trailing edge 72 (FIG. 1). Following solidification of the material poured into mold 304, the outer shell mold 302 may be broken away and the core 300, as well as any optional RMC 500, may then be removed from the solidified component 20 by, for example, caustic leaching or mechanical processes, to form the finished component 20. It should be appreciate that machining, surface treating, coating or any other desirable finishing operation may further finish the component 20.

During the removal process of the core 300 and/or the RMC 500, residual from the core 300 may remain within the component 20. However, as detailed above, the radiopaque particles 125 within the core 300 permit a film or digital X-ray, possibly a bench-top X-ray, to facilitate inspection of the component 20 for residual material 120 to confirm complete removal of the core 300. If residual material is detected, additional removal processes may be performed to ensure a properly finished component 20.

The use of the terms "a," "an," "the," and similar references in the context of description (especially in the context of the following claims) are to be construed to cover both the singular and the plural, unless otherwise indicated herein or specifically contradicted by context. The modifier "about" used in connection with a quantity is inclusive of the stated value and has the meaning dictated by the context (e.g., it includes the degree of error associated with measurement of the particular quantity). All ranges disclosed herein are inclusive of the endpoints, and the endpoints are independently combinable with each other. It should be appreciated that relative positional terms such as "forward," "aft," "upper," "lower," "above," "below," and the like are with reference to the normal operational attitude of the vehicle and should not be considered otherwise limiting.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason the appended claims should be studied to determine true scope and content.

What is claimed is:

1. A method of manufacturing a core for casting a component, comprising:
   manufacturing a core for at least partially forming an internal passage architecture of a component with a material including radiopaque particles; and
   inspecting the component via radiographic imaging at gamma/X-ray wavelengths to detect residual material subsequent to manufacture of the component.

2. The method as recited in claim 1, wherein the radiopaque particles include refractory metal oxide particles.

3. The method as recited in claim 1, wherein the radiopaque particles include at least one of Molybdenum Dioxide (MoO2), Zirconium Dioxide (ZrO2), tungsten trioxide, tantalum pentoxide, molybdenum silicide, tungsten silicide, elemental molybdenum, tantalum, chromium and tungsten.

4. The method as recited in claim 1, further comprising attaching a Refractory Metal Core to the core.

5. The method as recited in claim 1, wherein the core is produced by a molding process.

6. The method as recited in claim 1, wherein the core is transfer molded.

7. The method as recited in claim 1, wherein the core is injection molded.

8. The method as recited in claim 1, wherein the core is additively manufactured.

9. The method as recited in claim 1, further comprising forming an outer shell mold that contains the core, wherein a cavity is formed by the outer shell mold and the core, the cavity defining the component.

10. A method, comprising:
    removing a salt-based protective fill material including radiopaque particles from an internal passage architecture of a component; and
    inspecting the component via radiographic imaging at gamma/X-ray wavelengths to detect residual salt-based protective fill material through identification of the radiopaque particles.

11. The method as recited in claim 10, wherein the radiopaque particles include refractory metal oxide particles.

12. The method as recited in claim 10, wherein the radiopaque particles include at least one of Molybdenum Dioxide (MoO2), Zirconium Dioxide (ZrO2), tungsten trioxide, tantalum pentoxide, molybdenum silicide, tungsten silicide, elemental molybdenum, tantalum, chromium and tungsten.

13. The method as recited in claim 10, further comprising filling at least one of a multiple of cooling holes formed by the internal passage architecture with the material.

14. The method as recited in claim 13, further comprising removing the material from the at least one of the multiple of cooling holes formed by the internal passage architecture with a manual operation.

15. The method as recited in claim 14, further comprising filling the at least one of the multiple of cooling holes formed by the internal passage architecture with an Oxidation Resistant Braze (ORB).

16. The method as recited in claim 15, further comprising forming a cooling hole through the Oxidation Resistant Braze (ORB) subsequent to the filling the at least one of the multiple of cooling holes formed by the internal passage architecture with an Oxidation Resistant Braze (ORB).

17. A core for use in casting an internal passage architecture of a component, comprising:

a salt-based protective fill material with radiopaque particles dispersed therein, said radiopaque particles detectable via radiographic imaging at gamma/X-ray wavelengths.

18. The core as recited in claim 17, wherein the radiopaque particles include at least one of Molybdenum Dioxide (MoO2), Zirconium Dioxide (ZrO2), tungsten trioxide, tantalum pentoxide, molybdenum silicide, tungsten silicide, elemental molybdenum, tantalum, chromium and tungsten.

19. The core as recited in claim 17, wherein the radiopaque particles include refractory metal oxide particles.

20. The core as recited in claim 1, wherein the radiopaque particles are of a particle size between 0.0001 inches to 0.003 inches (0.0025 mm-0.076 mm) in diameter.

21. The core as recited in claim 1, wherein the core is manufactured of a material that is an alumina.

22. The core as recited in claim 1, wherein the core is manufactured of a material that is a silica-base ceramic fill.

23. The core as recited in claim 1, wherein the core is manufactured of a material that is a salt-based protective fill.

24. The core as recited in claim 23, wherein the salt-based protective fill is a water soluble material composed of a salt such as magnesium sulfate, tribasic potassium phosphate, or other such salt-based composition.

25. The core as recited in claim 23, wherein the salt-based protective fill is a water soluble material composed of a mixture of about 50 mol % of Na2CO3, about 20 mol % of NaCl, and about 30 mol % of KCl.

26. The core as recited in claim 23, wherein the salt-based protective fill has an upper temperature limit that is tuned by selection of the salt.

27. The core as recited in claim 26, wherein the salt-based protective fill comprises magnesium sulfate that will not melt until 2055° F. (1124° C.) and tribasic potassium phosphate will not melt until 2516° F. (1380° C.).

* * * * *